US008932844B2

(12) United States Patent
Astarita et al.

(10) Patent No.: US 8,932,844 B2
(45) Date of Patent: Jan. 13, 2015

(54) PROCESS FOR STIMULATING THE DEFENSE MECHANISM OF A PLANT USING A BACTERIAL EXTRACT ELICITOR

(71) Applicants: Leandro Vieira Astarita, Porto Alegre (BR); Fernando Rostirolla Dalmas, Porto Alegre (BR); Vera Aparecida Dus Poiatti, Sao Paulo (BR)

(72) Inventors: Leandro Vieira Astarita, Porto Alegre (BR); Fernando Rostirolla Dalmas, Porto Alegre (BR); Vera Aparecida Dus Poiatti, Sao Paulo (BR)

(73) Assignee: Uniao Brasileira de Educacao e Assistencia—Mantenedora da PUCRS, Porto Alegre (BR)

( * ) Notice: Subject to any disclaimer, the term of this patent is extended or adjusted under 35 U.S.C. 154(b) by 0 days.

(21) Appl. No.: 14/058,221

(22) Filed: Oct. 19, 2013

(65) Prior Publication Data

US 2014/0045691 A1 Feb. 13, 2014

Related U.S. Application Data

(62) Division of application No. 13/132,523, filed as application No. PCT/BR2009/000412 on Dec. 16, 2009.

(30) Foreign Application Priority Data

Dec. 16, 2008 (BR) ..................................... 0805370

(51) Int. Cl.

| | |
|---|---|
| *C12N 1/06* | (2006.01) |
| *A01N 63/02* | (2006.01) |
| *A01N 63/00* | (2006.01) |
| *A01G 13/00* | (2006.01) |
| *A01N 25/00* | (2006.01) |

(52) U.S. Cl.
CPC ............... *A01N 63/02* (2013.01); *Y10S 435/91* (2013.01)
USPC ........ 435/252.1; 435/910; 504/117; 504/118; 424/780; 424/405; 47/89

(58) Field of Classification Search

CPC ........................ C12N 15/8279; C12N 15/8281

See application file for complete search history.

(56) References Cited

U.S. PATENT DOCUMENTS

| | | | | |
|---|---|---|---|---|
| 6,326,016 | B2 * | 12/2001 | Moesinger | 424/405 |
| 7,374,786 | B2 * | 5/2008 | Hysmith | 424/773 |
| 2002/0066122 | A1 * | 5/2002 | Wei et al. | 800/279 |
| 2010/0330055 | A1 * | 12/2010 | Igarashi et al. | 424/93.45 |

OTHER PUBLICATIONS

Citri, Diagnostics, Eur. and Med. Plant Protection Org., 35:289-294, 2005.*
Firdous et al., Development of Hypersensitive Response by *Xanthomonas campestris* on *Lycopersicon esculentum* and *Solanum tuberosum* leaves, Pak. J. Bot., 39(6):2135-2139, 2007.*
Dunger et al., Participation of *Xanthomonas axonopodis* pv. *citri* hrp cluster in citrus canker and nonhost plant responses, Plant Pathology, 54:781-788, 2005.*
Vesy et al., LPS-Binding Protein and Phospholipid Transfer Protein Release LPS from Gram-Negative Bacterial Membranes, Infection and Immunity, vol. 68, No. 5: 2410-2417, 2000.*

* cited by examiner

*Primary Examiner* — Taeyoon Kim
*Assistant Examiner* — Srikanth Patury
(74) *Attorney, Agent, or Firm* — Laurence P. Colton; Smith Risley Tempel Santos LLC

(57) ABSTRACT

The invention induces an increase in the resistance of potato plants, without apparent toxicity for the plant. Preliminary experiments indicate that the increase in metabolism of plants efficiently fosters (above 60%) the reduction of the development of the pathogenic phytobacteria, *Erwinia carotovora*, one of the principal agents in causing diseases in potatoes.

6 Claims, 3 Drawing Sheets

US 8,932,844 B2

PROCESS FOR STIMULATING THE DEFENSE MECHANISM OF A PLANT USING A BACTERIAL EXTRACT ELICITOR

STATEMENT OF RELATED APPLICATIONS

This patent application is a divisional of and claims the benefit of U.S. patent application Ser. No. 13/132,523 entitled "Bacterial Extract Elicitor" having a filing date of 02 Jun. 2011, which is the Patent Cooperation Treaty National Phase in the United States of America of International Application No. PCT/BR2009/000412 having an International Filing Date of 16 Dec. 2009, which claims the benefit of Brazilian Patent Application No. PI0805370-7 having a filing date of 16 Dec. 2008.

FIELD OF THE INVENTION

This patent application relates to a bacterial extract with the capability to stimulate the metabolism responsible for plants self-defence, particularly plants belonging to the Solanum genus.

This invention also relates to a process for producing this extract and compositions comprising said extract, where such compositions are used in agriculture.

Finally, this invention relates to a process for stimulating plants self-defence comprising the use of a composition comprising the bacterial extract.

BACKGROUND OF THE INVENTION

About 75% of production losses in the world can be directly attributed to diseases (Agrios 1997). In this context, approximately 24% of world potato production is lost due to diseases caused by bacterias, with approximately 40% of losses sometimes occurring in developing countries (Oerke, 2006). In order to avoid losses, the use of agrochemicals is indispensable in agriculture. However, the use of these techniques for diseases control is increasingly questioned with regards to their impact on the environment and human health. So as to overcome this impasse, conventional improvements have developed cultivars that are more resistant to diseases. Nonetheless, resistant varieties to bacterial diseases are still rare (Yi et al., 2004).

Plant adaptation and resistance to diseases occur due to considerable alterations in cells metabolism, such the protein synthesis and defence molecules, induced through complex mechanisms involving the pathogens presence recognition.

The activation of latent resistance mechanisms in plants, by administering elicitor agents represents an alternative for the agricultural diseases control, without the use of substances with direct effects on phytopathogens and often toxic effects for humans, such as fungicides, bactericides and nematicides. According to Medeiros et al., (2003), contact between the pathogen and the host plant cell unleashes synthesis reactions of compounds that are toxic for the pathogen, imitating in a rudimentary human and animal immunological systems.

In some cases, it is difficult to determine if the plant response occurs before or after the pathogen recognition. However, generally when the plant is attacked by microorganisms it is capable of producing inhibiting molecules next to the penetration location, promoting growth inhibition of the pathogens.

Natural selection and the co-evolution of plants with pathogens have caused plants to select a series of defence mechanisms. As such, it is believed that the difference between resistance and susceptibility may be the result of time variations, cellular autonomy or the intensity of plants defence responses (Moraes, 1998).

The recognition of pathogens for activating defence responses in non-host plants, is probably determined by invariable standards in molecules associated with the pathogens, which are characteristic of all classes of microorganisms, thereby inducing signalling cascades, partially similar to those that mediate the innate immune responses in animals (Nürnberger e Lipka, 2005).

The term elicitor was originally used to refer to molecules and other stimuli that induce synthesis or accumulation of anti-microbial compounds (phytoalexins) in plant cells. Phytoalexins constitute a heterogeneous group of subsequently-formed substances, which do not contain nitrogen in their molecules, among which, (cyclical or non-cyclical) isoflavonoid, furanoacetylene or terpenoid compounds seem to be the most important (Romeiro, 2001). Currently, the term elicitor is used for molecules that stimulate some kind of self-defence mechanism in plants, such as the accumulation of anti-microbial phytoalexins, the inducing of cell death (hypersensitivity reaction) and the synthesis of proteins that inhibit degrading enzymes produced by pathogens (Hahn, 1996). Generally, elicitors are molecules on the surface of a pathogenic micro-organism of a plant, which, when applied in host or non-host plants, induce resistance reactions typical of the pathogen-plant system studied (Kortekamp and Zyprian, 2003). The location of the hosts receptors, which recognise the elicitors of the pathogens, is largely unknown. Studies indicate that these receptors exist in the plasma membrane or outside of it, while other appear to be located in intracellular areas (Hutcheson, 1998).

Plants react to a pathogen infection by inducing resistance of a long duration and a wide spectrum to subsequent infections. This resistance response induced against diseases has been known for many years under different names, such as acquired physiological immunity or induced resistance; here we will refer to it using the abbreviation SAR, from English, (Systemic Acquired Resistance) (Ryals et al., 1994).

The phenomenon of inducement of systemic resistance or systemic acquired resistance was defined as being the activation of resistance against diseases, induced systematically in plants, by a localised phytopathogen infection, or in response to the administration of different abiotic agents. Among said agents, we can cite β-aminobutyric acid (BABA), salicylic acid (SA) and the respective analogous, functional agents such as 2,6-dichloroisonicotinic acid (INA) and s-methyl ester from benzo-(1,2,3)-thiadiazole-7-carbothioic acid (acibenzolar-S-methyl, ASM) (Herbers et al, 1996; Guzzo, 2004). Furthermore, SAR can be induced by different molecules, such as carbohydrates, glycoproteins, proteins and lipids (Ricci et al., Hahn et al., 1996). These molecules can originate from extracellular lipopolysaccharides in bacteria, glycoproteins from the cell wall of pathogenic fungi, carbohydrates from the cell wall of non-pathogenic fungi and so forth (Hahn and Albershein, 1978; Koch et al, 1998; Coventry and Dubery, 2001). To this end, Wulff and Pascholati (1999), carried out the partial purification and biochemical characterisation of a glycoprotein elicitor present in the cell wall of *Saccharomyces cereviseae*, capable of inducing the synthesis of phytoalexins in weakened mesocotyls of sorghum.

In *Solanum tuberosum*, SAR can be induced by the components of the cell wall of hyphae of the fungus, *Phytophthora infestans*, such as Pep-13 oligopeptide (Halim, 2004), in which local and systemic oxidative burning occurs. As such, local treatment with the elicitor on the leaflets of compound leaves of a plant, induced sub-systemic, local oxidative burning, that is, in other untreated leaflets of the same leaves, besides systemic burning (Park et al., 1998; Vleeshouwers et al., 2000). In tissues that are distant from the inoculation site in *Arabidopsis* leaves with the avirulent pathogen, *Pseudomonas syringae*, SAR progressed more effectively in younger leaves and this response was associated with a large accumulation of salicylic acid (Zeier, 2005).

Various agents can induce defence metabolism in plants, fostering lasting protective reactions against a broad range of phytopathogens. These agents (products) represent a new generation of commercial agricultural defences that in general do not produce a direct effect on pathogens, but bring about a increase in plant resistance.

Since the discovery of the plant resistance inducer, s-methyl ester from benzo-(1,2,3)-thiadiazole-7-carbothioic acid (known as Acibenzolar-S-Methyl®, or ASM), a great advance has occurred in the development of products which take advantage of the activation capability of different defence mechanisms in plants. The commercial product, Acibenzolar-S-Methyl (ASM), whose commercial name is Actigard® (Europe) or Bion® (Brazil), produced by the company Novartis, was registered in Brazil for the cultivation of tomato, citruses and cocoa. ASM seems to operate by inducing the synthesis of a phytoalexin molecule (coumarin) and a rapid accumulation of phenolic compounds in barley plants, reducing the penetration of fungi in the leaves. Accordingly, the administering of ASM in wheat induces the synthesis of resistance proteins (PR proteins) in the plant.

Messenger®, produced by the company Eden Bioscience, is a commercial product whose active ingredient is a protein known as harpin, which was isolated and purified using the bacteria, *Erwinia amylovora*, and produced artificially, for commercial purposes, as *Escherichia coli*. This protein weighs 44 kDa and is highly stable at high temperatures, naturally being associated with the bacteria wall. After spraying the Messenger®, the harpin protein attaches to the receptor of the plant cell and unleashes defence responses approximately 5 to 10 minutes after its application, with the defence response being completed after three to five days (Eden Bioscience, 2002). The product is not toxic to animals and quickly deteriorates under the effect of solar radiation or through the action of decomposing organisms both on the surface of the plant and in soil.

Milsana®, produced by KHH BioSci Inc, made from leaf extract from the plant, *Reynoutria sachalinensis* (giant knotweed—Polygonaceae). The dry and ground plant material (5 g) is mixed with ethanol (100 ml) and sprayed on the plants. It was registered as a bio-pesticide in the USA in 2000 and is used with ornamental plants (greenhouse), helping in protecting against *Oidio* spp. and the grey mould, *Botrytis cinerea*. This plant extract induces the accumulation of PR proteins and phytoalexins, causing an increase in plant defence.

Cucumber plants (*Cucumis sativus*) treated with Milsana® increase their resistance against *Sphareotheca fuliginea*, fostering an increase in the plant of endogenous defence mechanisms such as an elevation in the activity of peroxidases, β-1,3-glucanases, as well as the production of glycosylated phenolic compounds, which are toxic for micro-organisms (Daayf et al., 1995). This compound has variable and dependent effects from the cultivar being protected. However, this compound is not toxic for animals and can foster protection results similar to those obtained when using conventional fungicide.

Oxycom®, produced by the company Redox Chemicals, is a combination of an inducer (peracetic acid) from the production of oxygen reactive species (Hammerschimidt et al., 2001) and a mix of nutrients. In species of bean plants, this product induces the expression of genes related to defence, codifying proteins involved in the metabolism of phenols and the thickening (reinforcement) of the cell wall, as well as that of peroxidases and protein extensines in tobacco (Anderson et al., 2001).

Neemazal®, produced by the company EID-Parry, is a product obtained from extracts of the plant Neem (*Azadirachta indica*), which has been marketed as insecticide. The active ingredient of the extract is a triterpene with a 5% concentration in the commercial product.

Ecolife 40®, produced by the company Quinabra, is made up of citrus bioflavonoids (vitamin P), ascorbic acid (vitamin C), lactic acid and citric acid, industrially obtained through the fermentation and/or extraction of organic substrates taken from citric plants, as well as polyphenols and phytoalexins. The product has various mechanisms of action, of which resistance inducement via the increase of phytoalexin synthesis seems to be one of the most important (Motoyama, 2001). The product is efficient in some pathosystems. Jayme et al. (1999) and Castro et al. (1999) highlight the efficiency of the product with regards the control of powdery mildew and rust in the bean plant. Similarly, Gasparotto et al. (2000), demonstrated that this product was efficient in the control of the disease black Sigatoka (*Mycosphaerella fijiensis*), displaying protection levels similar to those obtained with tebuconazole fungicide, with the advantage of not leaving residues on the fruits (Sanhueza, 2002).

Elexa® has as its active ingredient a carbohydrate molecule derived from chitin. In the USA, there are three products which contain chitin: Elexa® (0.95% chitosan); Hygra Yield Enhancing Seed Treating Agent (2.5% chitosan) and Yea Poly-D-Glucosamine Solution (2.5% chitosan). Chitosan is a polysaccharide which occurs mainly in animals from the Arthropoda phylum and its mechanism of action in plants is similar to that observed when a fungus attacks a plant. The pathogen is perceived by the recognition of chitin monomers, causing biochemical reactions that culminate in the expression of the Systemic Acquired Resistance (SAR). This product is sprayed on strawberry, tomato and apple crops, bringing about an increase in the plants' resistance.

Oryzemate®, produced by BioSafe, is used principally in rice farming as a fungicide agent. However, it was demonstrated that this product does not have a direct effect on rice pathogens, but it encourages an increase in the plant's resistance against micro-organisms. This product's ingredients include 2-sulphamoilbenzoato, saccharin and N-β-D-glucopyranosylsaccharin. This mix of molecules induces the expression of the defence protein PRR1, encouraging resistance against the pathogen, *Pyricularia oryzae*.

Extracts from bacterial cultivation can be used as biopesticides. According to the definition adopted by the United States Environmental Protection Agency (EPA), biopesticides are certain types of pesticides derived from natural materials such as animals, bacteria and certain minerals (www.epa.gov/pesticides/biopesticides). Although the EPA currently displays a numerous list of registered products such as biopesticides, including those which induce systemic resistance in plants, many other products that encourage plant resistance are not registered as biopesticides due to the high costs in registering a product such as pesticide (Anderson et al., 2006).

Printed sources on patents contain various documents related to elicitor compositions, of which the most relevant for the invention herein are described below.

The document, PI 0402152-5, consists of a biological control on yeast and fungi in stocked food or in the field by way of a process of predation carried out by yeast of the genus,

*Saccharomycopsis*. The document, PI 0402152-5, uses exotic live yeast originating from Canada, which are introduced directly over plants, or part of them, that must be preserved from the action of degrading micro-organisms or toxin producers.

The document, U.S. Pat. No. 5,968,504, uses the fungus *Gliocladium catenulatum* as a biological control agent through the competition and inhibition mechanism against the growth of pathogenic fungi.

The invention herein differs from the cited documents as it encourages an increase in plants' defence metabolism, without interacting directly with degrading microorganisms and microorganisms which cause diseases in plants. As such, the invention herein does not depend on the existence of the antagonistic ecological interaction, such as competition, parasitism, the production of antibiotics, and it does not entail the risk of the opportunist colonisation of animals and humans.

The document, PI 0418380-0A, consists of the use of a compound mixture of biological extracts, which when sprayed on plants encourage the inducement of resistance in plants against attacks from phytopathogenic *Xanthomonas*. The product consists of a mixture of extracts of non-phytopathogenic *Xanthomonas* spp., *Trichoderma harzianum* and the plant, *Yucca schidigera*. The product encourages inducement of the natural defence system of plants against the variety, *Xanthomonas* spp., and its variations.

The invention herein differs from the said document as it encourages resistance against a pathogen unrelated to the bacteria from which the extract originated. The invention herein consists of an extract containing *Xanthomonas axonopodis* pathovar *citri*, which, preferably sprayed on plants, plantlets and seeds, such as *Solanum tuberosum*, induces natural plant defences against bacteria and pathogenic fungi, preferably the bacteria, *Erwinia carotovora*, and the fungus, *Alternaria solani*, in plants of the Solanaceae family. The document, U.S. Pat. No. 6,242,420, refers to the use of a protein (molecular weight of 18 kDa) extracted and purified from cultures of the fungus, *Trichoderma virens*, and applied in the form of a solution on plants, plantlets and seeds.

The present invention differs from this document, as it uses an extract of *Xanthomonas axonopodis* pathovar *citri* containing both structures derived from the cell wall and cytoplasmic components.

Therefore, one can see that prior art does not describe or even suggest the objects of the invention herein, and as a result it meets patentability requirements.

SUMMARY OF THE INVENTION

In a first aspect the present invention provides a bacterial extract capable of promote and/or stimulate natural defences of plants against pathogens.

Is an object of this invention an extract comprising plasma membrane fragments, cell walls and cytoplasmic proteins obtained from a bacteria belonging to the genus *Xanthomonas*.

A further object of the invention is a composition comprising:
  a) An extract comprising fragments of plasma membrane, cell walls and cytoplasmic proteins obtained from a bacteria belonging to the genus *Xanthomonas*, and
  b) An acceptable vehicle.

In particular, the composition is applied on plants of agricultural interest, such as potato, and the vehicle can be the same medium for dilution of the extract.

In a second aspect, this invention provides a process for extract production from the cultivation and lysis of bacteria.

A further object of the present invention is a process comprising the steps of:
  a) Cultures of bacteria belonging to the genus *Xanthomonas* in a liquid medium;
  b) Lysis of cultivated bacteria, producing fragments of plasma membrane, cell walls and cytoplasmic proteins; and
  c) Extract dilution.

In a third aspect this invention describes a process for stimulating the defences of a plant comprising a stage of administering to a plant which need a stimulus to produce defences with a composition comprised of:
  a) An extract comprising fragments of plasma membrane, cell walls and cytoplasmic proteins obtained from a bacteria belonging to the genus *Xanthomonas*, and
  b) An acceptable vehicle.

These and other objects of the invention will be detailed in the following description.

DETAILED DESCRIPTION OF THE INVENTION

Figure 1:
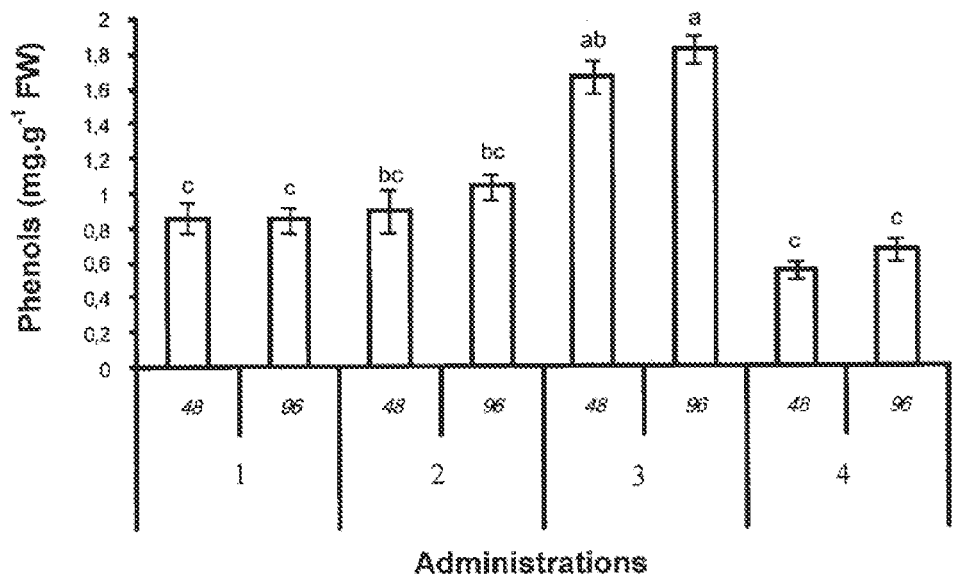
FIG. 1 illustrates the leaves of *S. tuberosum* analysed after multiple inoculations with bacteria suspensions (48 and 96 post-inoculation hours). Graph A displays the phenolic compounds and B displays the content of flavonoids. Different letters indicate significant differences (ANOVA, Turkey $p \leq 0.05$. Independent experiments were performed three times with similar results: 1—intact leaves; 2—water; 3—*X. axonopodis*; 4—*E. carotovora*.

The examples shown here have the sole aim of exemplifying one of the numerous results of the invention, however, without limiting it, as similar results are within the scope of the invention.

The advantage of the bacteria extract of present invention is the requirement of a low number of applications in plants (just once), promoting a high rate of immunisation for about to 60 days. Another advantage is the use of a biotic inducer (*Xanthomonas*) originating from the natural environment, which is used in the inducement of resistance in Solanum plants adapted to Brazilian conditions. This proximity between the inducer and the plant increases the chances of greater efficiency in immunisation.

In this context, the present invention serves to increase the resistance in potatoes against bacteria and fungi, thereby reducing the levels of agrotoxins employed in diseases control caused by these microorganisms.

The bacteria preferred of the present invention can lead the extract, are chosen from the genus *Xanthomonas*. Examples of preferred species include, but are not limited to, the species *Xanthomonas axonopodis* pv. *citri*, which are bacteria from the soil that cause disease in arugula and citrus plants (citrus canker). The agent used to prepare the product is preferably *Xanthomonas axonopodis*; any other pathogenic or non-pathogenic microorganism may be used.

Synonyms of the bacteria are following listed: *Pseudomonas citri* Hasse, *Xanthomonas citri* (Hasse) Dowson, *Xanthomonas citri* f. sp. *aurantifoliae* Namekata & Oliveira, *Xanthomonas campestris* pv. *Citri* (Hasse) Dye 1978, *Xanthomonas campestris* pv. *Aurantifolii* Gabriel et al., *Xanthomonas citri* (ex Hasse) nom. rev. Gabriel et al., *Xanthomonas axonopodis* pv. *Aurantifolii* Vauterin et al.

Cultures of *X. axonopodis* pv. *citri* can be obtained from citrus plants that are contaminated and presents symptoms of disease (citrus canker), characterised by the formation of oily, small, circular pustules with a brown colour on the abaxial surface of the infected leaves. Isolation plate allows the observation of the yellow-orange colonies coloration, typical of the genus. This isolation can be performed using nutritive agar according to the technique described by Meneguim et al. 2007.

Cultures of the bacteria, *X. axonopodis* pv. *citri*, were used to produce aquous extracts. The extracts of these bacteria were employed in the experiments in their raw form, without using any purification method or process.

The plants that will receives the extracts are cultivatable plants that are commonly found in agriculture. Examples of such plants include plants belonging the Solanaceae family, in particular belonging to the Solanum genus. The preferred species is *Solanum tuberosum*.

The extract is effective against bacteria and/or fungi that are recognised to be pathogenic in cultivable plants. Examples of such bacteria and/or fungi include, but are not limited to *Erwinia carotovora* subsp. *carotovora* that are soil bacteria, widely distributed in the environment, which cause diseases in a broad variety of olericultural plants, with the potato being the most affected by this pathogen. This bacterium causes soft rot and butt rot, affecting plants in the field, in the post-harvest phase and in the storage of tubers. *Erwinia carotovora* belong to a complex taxon, consisting of strains with broad phenotypic, biochemical and genetic variation and with different hosts.

Extraction Process

The extraction processes comprises the following steps:
a) Cultivation of bacteria belonging to the *Xanthomonas* genus in a liquid medium;
b) Lysis of the cultivated bacteria, producing fragments of plasma membrane, cell walls and cytoplasmic protein; and
c) Extract dilution;

Preferably, the process consists of all of the following steps:
1. Selection of the bacteria, *Xanthomonas* sp;
2. Cultivation of bacteria *Xanthomonas* sp, preferably *Xanthomonas axonopodis* pv. *citri* in a liquid medium;
3. Remove bacteria from the culture medium, preferably by centrifugation;
4. Resuspension of the bacteria and optical density adjustment of the bacterial solution ($DO_{600}$=1.00 Abs);
5. Lysis of the bacteria using physical and chemical media, preferably autoclaving at 121° C. for 20 min;
6. Dilution of the extract (5 mL extract/L)—the solvent can be water, organic solvents such as ethanol, methanol, inorganic solvents or combinations thereof;
7. Spraying leaves of the plants are protected (10 mL/plant).

The composition comprising the extract is a composition for agricultural use, and comprises:
a) An extract comprising fragments of plasma membrane, cell walls and cytoplasmic proteins obtained from a bacteria belonging to the genus *Xanthomonas*, and
b) An acceptable vehicle.

An acceptable vehicle is any vehicle that allows the distribution of the composition. Furthermore, the composition can be in liquid or solid form. The vehicle can even be the dilution medium of the extract.

The product developed consists of an extract of the bacteria *Xanthomonas axonopodis* pathovar *citri*, preferably prepared in water; other organic or inorganic solvents can be used. The concentration of the extract can vary from 0.1 to 1.5 Abs in 600 nm. The extract consists of cell walls and cytoplasmic components fragments of the bacteria. The extract is preferably prepared by utilising ultrasound and 3 cycles of 24 h of freezing-defrosting (−20° C.); other physical and chemical mediums can be utilised to encourage bacterial lysis and obtain the extract.

The product developed has a concentration of 5 mL of the raw extract prepared in a liquid medium. 10 mL of the product is used for each plant, preferably using a spraying method directly on the plant or the roots; a powder-form or any other form can be used. It can be used in a pure form or in combination with fungicides or other biotic and abiotic factors that enhance the induction of metabolism related to defense. Its use can also occur with surfactant agents or promoting adherence to the plant.

EXAMPLE 1

*Erwinia carotovora* subsp. *carotovora* bacteria were used to assess effectiveness in resistance tests of potato plants after the application of the resistance-inducing product.

Potted plants of *S. tuberosum* with an age of seven weeks, which were kept in a greenhouse, were utilised. Bacterial suspensions with *Xanthomonas axonopodis* pv. *citri* and *Erwinia carotovora* subsp. *carotovora* were prepared with $H_2O$ (Abs 0.3-0.4 to 600 nm). The inoculations of basal, intermediate and apical leaves from branches were performed with a syringe with a needle on the abaxial surface of the terminal leaflet.

The time between application of the product to induce plant resistance metabolism and the trial with the pathogen was 5 days. Just one application was performed on the plants.

Samples of different leaves (0.5 g each) were taken of the treated plants and then extraction was performed by macerating the samples in 80% methanol, which was utilised to quantify the phenolic compounds (Folin-Ciocaulteau method) and flavonoids (aluminium nitrate and potassium acetate).

The determination of enzyme activities was performed in extracts obtained by macerating the leaves in a cold phosphate buffer. For the activities of PPO enzymes, the difference in absorbance was evaluated in the buffer with chlorogenic acid substrate. The results were submitted to a one-way analysis of variance ($p \leq 0.05$) and to a Tukey test.

After inoculating the *X. axonopodis* and *E. carotovora* bacteria, the plants were observed to check the development of disease symptoms and the samples were taken from the leaves to evaluate the markers levels of the of secondary metabolism plant-defence (phenolic compounds, flavonoids, enzyme activity of poliphenoloxidases and peroxidases).

Can observe the formation of a defence response in the regions of the leaf which were inoculated with this bacteria. This fact indicated that potato plants have the capacity to recognise the presence of *X. axonopodis*, inducing a defence response that hinders this bacteria development in their tissues. The inoculation of *Erwinia carotovora* cultures in potato leaves caused the development of disease symptoms and subsequent plants death. This result indicated that this plant species has no defence mechanisms against pathogenic phytobacteria attack. Its inability to defend the plant due to lack/low sensitivity of specific receptors on cells that allow the recognition of the phytobacteria.

Plants inoculated with *E. carotovora* do not display biochemical defence responses, such as a rise in the levels of phenolic compounds (FIG. 1A). However, the presence of *X. axonopodis* encouraged a large increase in compounds related to plant defence, indicating the inducement of a defence response. As such, the levels of flavonoids in the leaves of the potato plant displayed a large and stable increase when they were inoculated with *X. axonopodis* (FIG. 1B). The increase in levels of both phenolic compounds and flavonoids represent plant-defence mechanisms against the attack of microorganisms.

Figure 2A:
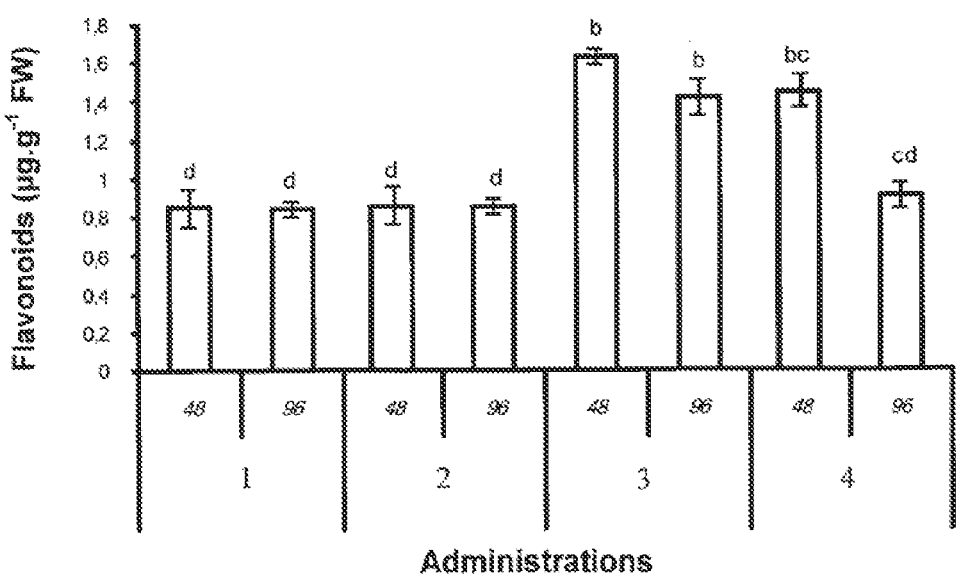
FIG. 2 demonstrates the activity of polyphenol oxidase on leaves of *S. tuberosum* analysed after inoculation with bacteria suspensions (48 and 96 post-inoculation hours). Different letters indicate significant differences (ANOVA, Turkey $p \leq 0.05$. Independent experiments were performed three times with similar results: 1—intact leaves; 2—water; 3—*X. axonopodis*; 4—*E. carotovora*.
Figure 2B:
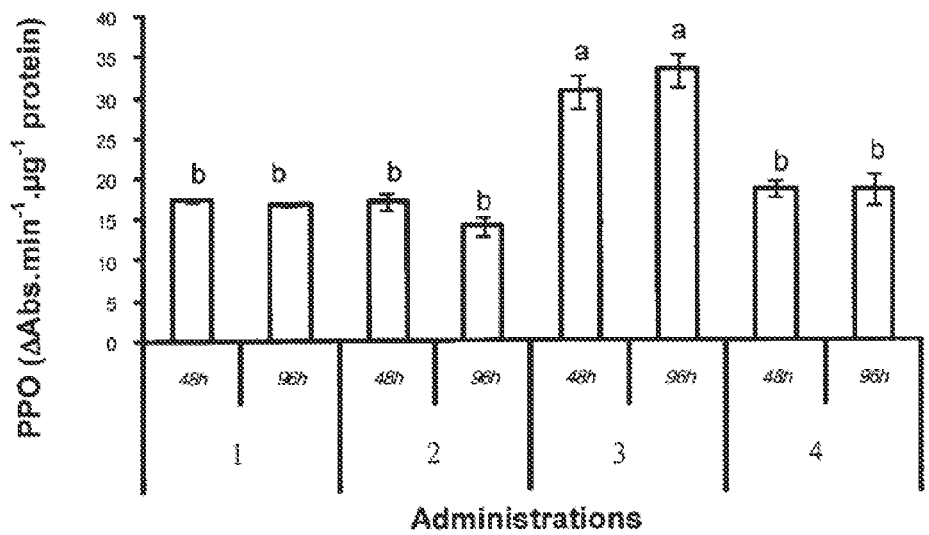

Upon analysing the activity of enzymes related to the plant-defence mechanism, one observes that *X. axonopodis* encourages a significant increase in activities (FIG. 2). Among the bacteria utilised in the experiments, it was observed that *X. axonopodis* fostered an increase in phenols and flavonoids and an increase in the activities of PPOs. The results indicate that this phytobacteria operates as a metabolism inducer related to defence in the potato cultivar.

The results indicate that *X. axonopodis* induced an efficient increase in metabolism related to plant defence.

EXAMPLE 2

To assess the efficiency of the *Xanthomonas axonopodis* extract in increasing of potato plants resistance against pathogenic phytobacteria, autoclaved extracts of *X. axonopodis* were applied and subsequently inoculated with pathogenic bacteria.

Potato plants with approximately 12 weeks were utilised. Bacterial suspensions with *Xanthomonas axonopodis* pv. *citri* were prepared with $H_2O$ (Abs 0.3-0.4 to 600 nm). The bacterial suspensions were autoclaved for 20 min at 120° C. and 1 atm. The plants were sprayed just once with autoclaved suspensions of *X. axonopodis* bacteria or sprayed with sterile distilled water.

Figure 3:
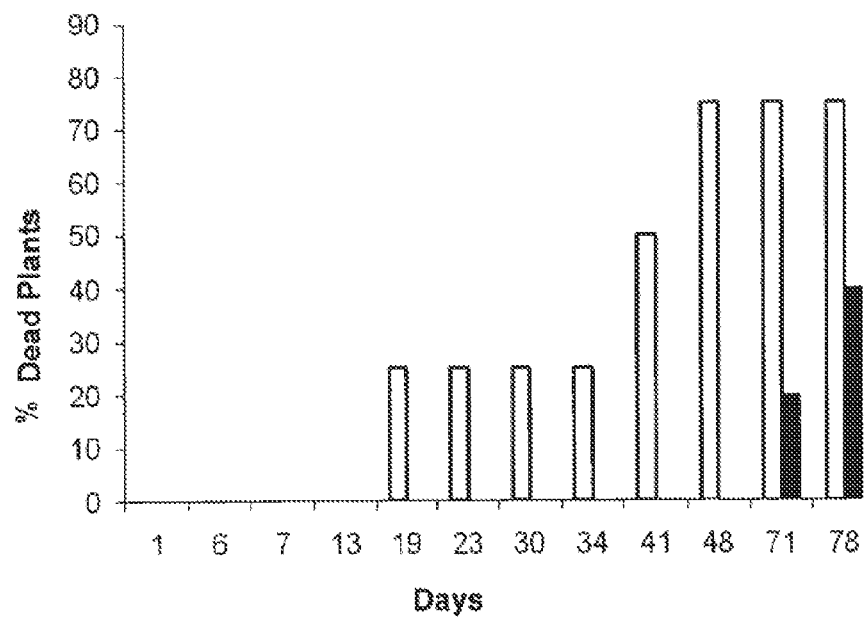
FIG. 3 demonstrates the percentage of deaths of potato plants sprayed with autoclaved extracts of *Xanthomonas axonopodis* or sprayed with water (Control). After spraying, all the plants were inoculated with the pathogen, *Erwinia carotovora*. Control (□); Extract (■)

After five days of spraying, all the plants were inoculated with a culture of *Erwinia carotovora*, pathogenic phytobacteria from potato plants. This inoculation followed the same methodology as was used previously, leaves were inoculated with a syringe without needle. In this experiment it was observed that previous exposure by the plants to the autoclaved extract with *Xanthomonas axonopodis* promoted a 60% reduction in death after 78 days of inoculation in which the pathogenic phytobacteria, *Erwinia carotovora*, was applied directly to the leaves (FIG. 3).

The control administrations (sprayed with water) presented a 75% death-rate 78 days after inoculation with *E. carotovora*.

These results make it evident the protective effect that *X. axonopodis* cultivation possess in reducing subsequent attacks from phytobacteria and, possibly, from other pathogenic microorganisms, evidenced by the deferment of deaths and the lowering of the plants death rate. In this experiment, the extract of *X. axonopodis* was applied only once; one could increase the number of applications in order to further increase the level of protection of plants.

The efficiency of the autoclaved extracts of *X. axonopodis* was compared with the commercial product, Bion® 500 WG (Syngenta Protecção de Cultivos Ltda. company), utilised as a resistance inducer in potatoes (Class: Plant Activator), so as to assess the percentage of induced protection. For this reason, autoclaved extracts of *X. axonopodis*, Bion® solution (concentration of 0.0005 g/plant) or water were applied and subsequently inoculation was performed with the pathogenic bacteria, *Erwinia carotovora*. Only one spray with resistance inducers or water was performed.

Figure 4:
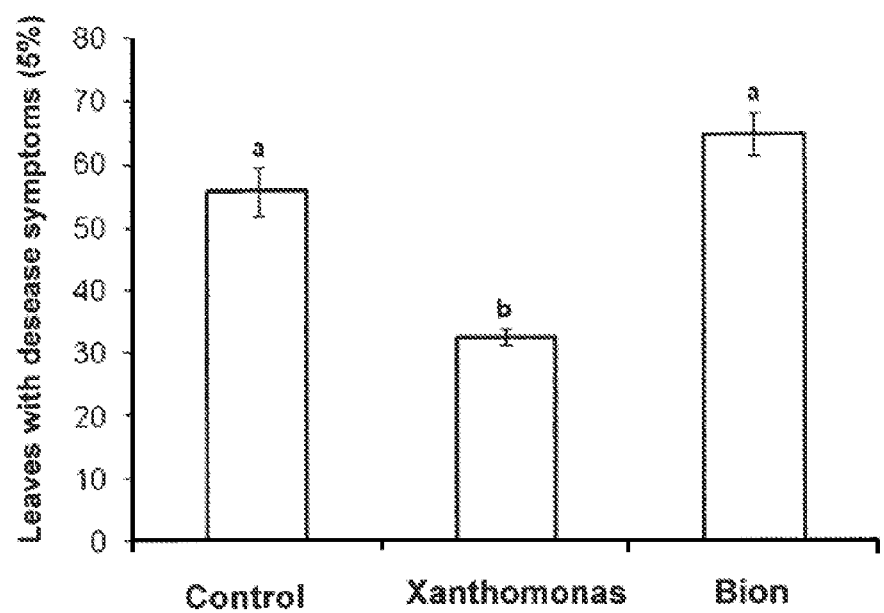
FIG. 4 demonstrates the percentage of potato plant leaves with symptoms of the disease caused by the phytobacteria, *Erwinia carotovora*. The plants were previously sprayed once with an autoclaved extract of *Xanthomonas axonopodis*, with the resistance inducer Bion® or sprayed with water (control). After spraying all the plants, they were inoculated with the pathogen *Erwinia carotovora*. The analysis of the results was performed 72 days after the inoculation with the pathogen.

When comparing the effect of the immunisation of the *Xanthomonas* extract with the protection effect fostered by the commercial product, Bion®, it can be verifyed that the bacteria extract was significantly superior to the other administrations (FIG. 4).

These results reveal that the *Xanthomonas* extracts are highly efficiently at inducing an increase in potato resistance. The mechanism or exact means of this response is not known, but it must involve the stimulation of the plant's defence mechanisms and may include the synthesis route of phenolic compounds. This high level of efficiency may also be related to the use of the complex extract instead of a single molecule such as acibenzolar-S-methyl (Bion®), thereby enabling the concurrent activation of various means of response in plants.

The invention claimed is:

1. A process for stimulating the defense mechanism of a plant belonging to the Solanaceae family, comprising administering to the plant a composition comprising:
    a) a denatured bacterial extract comprising fragments of plasma membrane, cell walls, and cytoplasmic proteins obtained by autoclaving bacteria selected from the group consisting of *Xanthomonas citri, Xanthomonas campestris, Xanthomonas axonopodis*, and combinations thereof; and
    b) an acceptable vehicle;
    wherein the composition is sprayed over a plant.

2. The process according to claim 1, wherein the extract is applied to a portion of the plant selected from the group consisting of leaves of the plant, roots of the plant, and combinations thereof.

3. The process according to claim 1, wherein the composition is in solid or liquid form.

4. The process according to claim 1, further comprising culturing the bacteria in a vehicle in liquid form as a cultivation medium prior to forming the composition.

5. The process according to claim 1, wherein the composition further comprises an agent that promotes adherence of the composition to the plant.

6. The process according to claim 1, wherein the plant is *Solanum tuberosum*.

* * * * *